United States Patent [19]

Nagura et al.

[11] 4,345,089

[45] Aug. 17, 1982

[54] RECOVERY OF AROMATIC CARBOXYLIC ACID OR ESTER THEREOF FROM RESIDUE FRACTION OF OXIDATION OR ESTERIFICATION REACTION MIXTURE

[75] Inventors: Kenji Nagura; Shinichi Takeda; Koshi Namie; Takao Fujii; Michio Yamamoto, all of Matsuyama; Seiichi Yokoyama, Tokyo, all of Japan

[73] Assignee: Hercofina, Wilmington, N.C.

[21] Appl. No.: 144,756

[22] Filed: Apr. 28, 1980

[30] Foreign Application Priority Data

Jan. 24, 1977 [JP] Japan .................................. 52-5748
Jan. 24, 1977 [JP] Japan .................................. 52-5749

Related U.S. Application Data

[63] Continuation of Ser. No. 870,800, Jan. 19, 1978, abandoned.

[51] Int. Cl.$^3$ ...................... C07C 67/00; C07C 51/42

[52] U.S. Cl. .................................... 560/77; 560/101; 560/102; 560/103; 562/487; 562/490; 562/492; 562/494

[58] Field of Search ............... 562/487, 490, 492, 494; 560/77, 101, 102, 103

[56] References Cited

U.S. PATENT DOCUMENTS 3,522,298  7/1970  Bryant et al. ...................... 562/412
3,845,100  10/1974  Kusak ................................. 562/412

*Primary Examiner*—Alan Siegel
*Attorney, Agent, or Firm*—George H. Hopkins

[57] ABSTRACT

Disclosed is a process for the recovery of aromatic carboxylic acid or ester thereof from the residue fraction of the oxidation or esterification reaction mixture resulting from the oxidation or oxidation and esterification of an aromatic compound having at least one methyl or formyl group directly bonded to a ring carbon atom. The process comprises treating the residue fraction with hydrogen and a hydrogenation catalyst.

22 Claims, No Drawings

RECOVERY OF AROMATIC CARBOXYLIC ACID OR ESTER THEREOF FROM RESIDUE FRACTION OF OXIDATION OR ESTERIFICATION REACTION MIXTURE

The application is a continuation of the copending application, Ser. No. 870,800, filed Jan. 19, 1978, and now abandoned.

This invention relates to a process for preparing aromatic carboxylic acids of their methyl esters in increased yields.

More specifically, the invention relates to a process for preparing an aromatic carboxylic acid or its methyl ester in increased yields which comprises oxidizing at least one aromatic compound having at least one methyl or formyl group directly bonded to a ring carbon atom of the aromatic ring in the liquid phase with molecular oxygen or a gas containing molecular oxygen in the presence of a heavy metal catalyst to form an aromatic carboxylic acid and if desired, esterifying the oxidation product containing the aromatic carboxylic acid; wherein at least a part of the resulting aromatic carboxylic acid or its methyl ester is separated from the oxidation reaction product or its methyl-esterification product, and the resulting by-products having higher molecular weights than the aromatic carboxylic acid or its methyl ester (to be referred to as "high-molecular-weight by-products") are contacted with hydrogen in the presence of a hydrogenation catalyst.

Suitable aromatic compounds having at least one methyl or formyl group directly bonded to a nuclear carbon atom of the aromatic ring (to be referred to as "starting aromatic compounds") are aromatic compounds containing a benzene, naphthalene or biphenyl ring, those containing a benzene ring being especially suitable. Examples of suitable starting aromatic compounds are listed below.

(A) Toluene, xylene (especially p-xylene), tolualdehyde (especially p-tolualdehyde), and toluic acid (especially p-toluic acid).

(B) Methyl toluate (especially methyl p-toluate).

(C) α- or β-Methyl naphthalene, and dimethyl naphthalene (especially 2,6- or 2,7-dimethylnaphthalene).

(D) Dimethyl biphenyl (especially 4,4'- or 3,3'-dimethyl biphenyl).

Numerous methods have been known to oxidize these starting aromatic compounds with molecular oxygen or a gas containing molecular oxygen (such as air) to produce the corresponding aromatic carboxylic acids. The present invention is directed particularly to those methods which involve oxidizing the starting aromatic compounds in the liquid phase with molecular oxygen or a gas containing molecular oxygen in the presence of heavy metal catalysts. These methods have the great advantage that neither an alkanoic acid solvent such as acetic acid nor a halogen compound promotor such as bromine, hydrogen bromide, ammonium bromide or sodium bromide is used. Specific examples of these oxidizing methods heretofore known include the following.

(1) Oxidation of toluene
Hydrocarbon Processing, Vol. 43, No. 11, pp. 174;
Hydrocarbon Processing, Nov. 1970, pp. 141–142; and
British Pat. No. 1,430,830.

(2) Oxidation of p-xylene or p-toluic acid
British Pat. No. 1,234,009;
U.S. Pat. No. 3,883,584; and
U.S. Pat. No. 3,873,611.

(3) Oxidation of methyl toluate
British Pat. No. 727,989.

(4) Oxidation of a mixture of p-xylene and methyl p-toluate:
British Pat. No. 809,730;
British Pat. No. 1,313,083; and
U.S. Pat. No. 3,890,374.

(5) Oxidation of a mixture of p-tolualdehyde and methyl p-toluate:
Japanese Patent Publication No. 23493/65

These methods (1) to (5) can be applied to the production of aromatic dicarboxylic acids other than those described above but contemplated by this invention.

The aromatic carboxylic acids or their methyl esters are useful as various materials or intermediates. Above all, benzoic acid is useful as a raw material for ε-caprolactam, phenol, terephthalic acid and dyestuffs, and as a food additive. Terephthalic acid and dimethyl terephthalate are very useful compounds as starting materials for the production of fiber- and film-forming polyesters. It is known that 2,6- and 2,7-naphthalenedicarboxylic acid or 4,4'- or 3,3-diphenyldicarboxylic acid is useful as a raw material for aromatic polyamides or aromatic polyesters.

According to the present invention, the aromatic compound is oxidized with molecular oxygen or a gas containing molecular oxygen in the liquid phase in the presence of a heavy metal catalyst. The desired carboxylic acid is separated from the resulting oxidation product, or the oxidation reaction product is esterified with methanol to obtain a methyl-esterification product from which the methyl ester of the aromatic carboxylic acid is separated. Thus, the aromatic carboxylic acid or its methyl ester can be separated. High-molecular-weight by-products formed by the oxidation reaction or methyl-esterification is contained in the residue left after separating the desired aromatic carboxylic acid or its methyl ester from the oxidation reaction product or its methyl-esterification product.

The residue is either discarded or used as a part of the fuel. Any method which could recover the aromatic carboxylic acid or its methyl ester or precursors of these from the residue would have a very great commercial value.

The recovery of useful compounds from the residue has been attempted for example in a process which comprises oxidizing p-xylene and/or methyl p-toluate in the presence of a heavy metal catalyst, esterifying the resulting oxidation product with methanol, separating dimethyl terephthalate and lower boiling intermediates from the esterification product, and recovering dimethyl terephthalate and its precursors from the distillation residue which is itself valueless. Specific examples of such a process are:

(i) Method in which the distillation residue is heated to a temperature of 260° to 400° C. (British Pat. No. 1,442,913).

(ii) Method in which the distillation residue is treated with methanol at a temperature of 260° to 400° C. (DT-OS No. 2,327,773).

According to these prior methods (i) and (ii), however, the yields of the aromatic carboxylic acid methyl ester and its useful precursors prepared from the distillation residue are not sufficient.

It is an object of this invention therefore to provide a process of preparing and recovering an aromatic carboxylic acid or its methyl ester or useful precursor convertible to these compounds from the high-molecular-weight by-products at a higher rate of reaction and in higher yields than the aforesaid conventional methods of treating the high-molecular-weight by-products to obtain the desired aromatic carboxylic acid or its methyl ester or useful precursors convertible to these compounds.

Another object of this invention is to provide a process which comprises treating the high-molecular-weight by-products to prepare and recover the aromatic carboxylic acid or its precursors convertible thereto as methyl esters of these in high yields.

Still another object of this invention is to provide a process of preparing the aromatic carboxylic acid or its methyl ester or precursors of these at a high rate of reaction from the high-molecular-weight by-products while inhibiting the formation of by-product coloring materials.

Still other objects and advantages of this invention will become apparent from the following description.

According to the present invention, the above objects and advantages can be achieved by a process for preparing an aromatic carboxylic acid or its methyl ester, which comprises (1-A) oxidizing at least one aromatic compound (starting aromatic compound) having at least one methyl of formyl group directly bonded to a ring carbon atom of the aromatic ring in the liquid phase with molecular oxygen or a gas containing molecular oxygen in the presence of a heavy metal catalyst to form an aromatic carboxylic acid, and (1-B) if desired, esterifying the oxidation product containing the aromatic carboxylic acid [first step]; wherein (2) at least a part of the resulting aromatic carboxylic acid or its methyl ester is separated from the oxidation reaction product or its methyl-esterification product [second step], and (3) the resulting by-products having higher molecular weights than the aromatic carboxylic acid or its methyl ester are contacted with hydrogen in the presence of a hydrogenation catalyst to convert at least a part of the by-products to the aromatic carboxylic acid or its methyl ester or precursors of any of these which are then recovered [third step].

The invention is described in more detail hereinbelow.

[Starting Aromatic Compounds]

At least one of the aromatic compounds having a benzene, naphthalene or biphenylene ring such as exemplified in (A), (B), (C) and (D) above is used. Of these compounds, aromatic compounds having a benzene ring are especially suitable. Above all, toluene, p-xylene, p-toluic acid, p-tolualdehyde, methyl p-toluate, a mixture of p-xylene and methyl p-toluate, and a mixture of p-tolualdehyde and methyl p-toluate are preferred.

[First Step of the Process of the Invention]

The first step of the process of this invention is either step (1-A) alone or both steps (1-A) and (1-B). The method of producing an aromatic carboxylic acid by oxidizing the starting aromatic compound in the liquid phase with molecular oxygen or a gas containing molecular oxygen in the presence of a heavy metal catalyst in accordance with the step 1-A of this invention is known. The method of methyl-esterification of the resulting oxidation reaction product in accordance with step 1-B of this invention is also known.

In the present invention, high-molecular-weight by-products may be obtained directly from the oxidation product of step 1-A in accordance with the second step of the invention. If desired, the oxidation product obtained by step 1-A may be methyl-esterified in accordance with step 1-B, and high-molecular-weight by-products may be obtained in accordance with the second step from the methyl-esterification product.

The procedures of steps 1-A and 1-B are well known, and will be only briefly described below.

(1) Oxidation of toluene

Benzoic acid is produced on a large commercial scale by oxidation of toluene. Almost all of methods for benzoic acid production involve the oxidation of toluene in the liquid phase with a gas containing molecular oxygen in the presence of a heavy metal catalyst, especially a cobalt compound catalyst in the absence of an alkanoic acid solvent and a halogen compound promotor (see Hydrocarbon Processing, Vol. 43, No. 11, p. 174 and Hydrocarbon Processing, November 1970, pp.141–142). As an improvement of these methods, it was also proposed to obtain benzoic acid in a higher yield by using an oxidation catalyst comprising (A) a manganese compound at least partially soluble in the oxidation reaction system and (B) a cobalt compound at least partially soluble cobalt in the oxidation reaction system, or a catalyst comprising (A) the manganese compound and (C) a nickel compound at least partially soluble in the oxidation reaction system (see British Pat. No. 1,430,830).

(2) Oxidation of p-xylene or p-toluic acid

A method for producing terephthalic acid has previously been well known which comprises oxidizing p-xylene with a gas containing molecular oxygen in the presence of a heavy metal catalyst in the liquid phase in the absence of an alkanoic acid solvent and a halogen compound promotor. British Pat. No. 1,234,009 states that a heavy metal compound such as a cobalt or manganese compound can be used as the oxidation catalyst. Methods have also been proposed in which terephthalic acid is produced at a higher rate of formation by using an oxidation catalyst consisting essentially of (A) a manganese compound at least partially soluble in the oxidation reaction system and (B) a cobalt compound (U.S. Pat. No. 3,883,584) or an oxidation catalyst consisting essentially of (A) a manganese compound at least partially soluble in the oxidation reaction system and (C) a nickel compound (U.S. Pat. No. 3,873,611).

(3) Oxidation of methyl p-toluate

A method for producing dimethyl terephthalate by oxidizing methyl p-toluate in the liquid phase with a gas containing molecular oxygen in the presence of a heavy metal catalyst to form an oxidation reaction product containing monomethyl terephthalate, and esterifying the product with methanol is well known as the Witten process or the Witten-Hercules process, and described in detail in British Pat. No. 727,989.

(4) Oxidation of a mixture of p-xylene and methyl p-toluate

A method for obtaining dimethyl terephthalate which comprises oxidizing a mixture of p-xylene and methyl p-toluate with a gas containing molecular oxygen in the liquid phase in the presence of a heavy metal catalyst in the absence of an alkanoic acid solvent and a halogen compound promoter, and esterifying the resulting oxidation product with methanol is also called the Witten process or the Witten-Hercules process same as in method (3) above. Dimethyl terephthalate is produced in great quantities on a commercial scale by this method. Heretofore, in the oxidation reaction in the Witten process, heavy metal compounds such as cobalt compounds or manganese compounds have been known as catalysts (British Pat. No. 809,730). Recently, a method which involves using an oxidation catalyst comprising (A) a manganese compound soluble at least partially soluble in the oxidation reaction system and (B) a cobalt compound at least partially soluble in the oxidation reaction system (British Pat. No. 809,730), and a method which involves using an oxidation catalyst comprising (A) the manganese compound and (C) a nickel compound at least partially soluble in the oxidation reaction system (U.S. Pat. No. 3,890,374) were suggested.

In the Witten process, dimethyl terephthalate can also be obtained by using p-tolualdehyde instead of the p-xylene, oxidizing a mixture of it with methyl p-toluate, and then methyl-esterifying the resulting oxidation reaction product.

The aforesaid methods for producing aromatic carboxylic acids or their methyl esters are only illustrative, and do not limit the process of this invention in any way.

We have found however that greater amounts of an aromatic carboxylic acid or its methyl ester or precursors of these can be recovered from the high-molecular-weight by-products by using a heavy metal catalyst containing at least a manganese compound soluble at least partially in the oxidation reaction system in the production of aromatic carboxylic acids or methyl esters thereof. In particular, greater effects can be obtained by using a heavy metal catalyst which contains at least (A) a manganese compound at least partially soluble in the oxidation reaction system and (B) a cobalt compound at least partially soluble in the oxidation reaction system, or a heavy metal catalyst which contains at least (A) a manganese compound at least partially soluble in the oxidation reaction system and (C) a nickel compound at least partially soluble in the oxidation reaction system.

[Second Step]

The second step itself of this invention which comprises separating substantially all or a part (for example, at least 50% by weight, preferably at least 70% by weight) of an aromatic carboxylic acid or its methyl ester as a main product from the oxidation reaction product or its methyl esterification product to obtain by-products having higher molecular weights than the aromatic carboxylic acid or its methyl ester (high-molecular-weight by-products) is already known in relation to the oxidation reaction or the methyl-esterification reaction in the first step.

When terephthalic acid is produced from p-xylene or benzoic acid from toluene by an oxidation reaction, a suitable amount of the starting aromatic compound such as p-xylene or toluene is added, if desired, to the oxidation reaction product, and the mixture is cooled to precipitate the aromatic carboxylic acid which is separated and recovered by any desired solid-liquid separating method. On the other hand, the starting aromatic compound such as xylene or toluene is separated by a suitable means such as distillation from the liquid layer resulting from the solid-liquid separation, thereby affording a residue containing high-molecular-weight by-products.

Alternatively, water is added to the oxidation reaction product to move the aromatic carboxylic acid as a main product of the oxidation reaction (for example, benzoic acid, toluic acid, or terephthalic acid) to the aqueous layer. The aqueous layer is then separated from the organic layer (oil layer), and cooled to precipitate the desired aromatic carboxylic acid which is separated and recovered. On the other hand, a residue containing high-molecular-weight by-products can be obtained by separating the starting aromatic compound from the oil layer by a suitable means such as distillation.

In the case of the methyl-esterification reaction product, substantially all or a part of the desired methyl ester of aromatic carboxylic acid (such as dimethyl terephthalate or methyl p-toluate) and lower boiling components (for example, the unreacted starting aromatic compound and low-boiling reaction products) is separated and recovered by distillation to obtain a distillation residue. Since the distillation residue contain high-molecular-weight by-products to be treated by the present invention, the resulting residue can be directly submitted to the third step to be described below in detail.

When the crude methyl ester of aromatic carboxylic acid obtained by distillation in the above-mentioned procedure is purified by a usual recrystallization technique, the recrystallization residue also contains by-products having higher molecular weights than the methyl ester. The recrystallization residue may, as such or in combination with the distillation residue, be subjected to the third step of this invention as high-molecular-weight by-products.

Whilst the basic method for obtaining high-molecular-weight by-products to be treated by this invention has been described hereinabove, it should be understood that the invention is in no way limited by this method. The process of this invention can be applied to any by-products having higher molecular weights than the aromatic carboxylic acid or its methyl ester which are obtained by separating at least a part, preferably at least 50% by weight, especially preferably at least 70% by weight, of the aromatic carboxylic acid or its methyl ester from the oxidation reaction product or its methylesterified product of the first step, or any compositions containing such by-products.

The constituents and proportions of the high-molecular-weight by-products are not known in detail. However, high-molecular-weight by-products obtained for example, by the Witten process which comprises oxidizing a mixture of p-xylene and methyl p-toluate and methylesterify the product to produce dimethyl terephthalate are presumably a mixutre of a variety of high-molecular-weight compounds including biphenyl compounds such as dimethyl 4,4'-biphenyldicarboxylate or trimethyl 2,4',5-biphenyltricarboxylate; benzocoumarin compounds such as dimethyl 3,4-benzocoumarindicarboxylate; and benzyl benzoate compounds such as dimethyl 4,4'-benzylbenzoatedicarboxylate. It is presumed that in addition to these compounds, great quantities of a higher-molecular-weight compound containing at least 3 benzene rings per molecule or a colored pitch-like high-molecular-weight compound of an unknown structure also exist in the by-product mixture. The high-molecular-weight by-product mixture obtained in the production of terephthalic acid by oxidizing p-xylene presumably contains biphenyl compounds such as 4,4'-biphenyldicarboxylic acid or 2,4',5-biphenyltricarboxylic acid, benzocoumarin compounds such as 3,4-benzocoumarindicarboxylic acid, benzyl benzoate compounds such as 4,4'-benzylbenzoatedicarboxylic acid, higher molecular weight compounds, and higher-molecular-weight compounds of unknown structures. The high-molecular-weight by-product mixture obtained in the production of benzoic acid by oxidizing toluene presumably contains biphenyl compounds such as biphenyl and biphenylcarboxylic acid, various complicated compounds such as diphenylethane and benzyl benzoate, higher molecular weight compounds, and high-molecular-weight compounds of unknown structures.

The details of the composition of high-molecular-weight by-product mixture obtained in the production of an aromatic carboxylic acid obtained by oxidizing another starting aromatic compound or its methyl ester obtained by esterifying the oxidation product with methanol are not known. Such by-product mixture presumably contains compounds having skeletons similar to those of the residues obtained in the production of dimethyl terephthalate, terephthalic acid, or benzoic acid described hereinabove, higher molecular weight compounds containing at least three aromatic rings per molecule, and colored pitch-like high-molecular-weight compounds of unknown structures.

[Third Step]

In the process of this invention, the high-molecular-weight by-products are then contacted with hydrogen in the presence of a hydrogenation catalyst to convert at least a part of the by-products to the aromatic carboxylic acid or its methyl ester or precursors of these which are then recovered.

This step enables the desired aromatic carboxylic acid or its methyl ester or useful precursors of any of these to be formed in higher yields than in the case of treating them by the method disclosed in British Pat. No. 1,442,913 or DT-OS No. 2,327,773 cited hereinabove.

A process has been known previously which comprises oxidizing a mixture of p-xylene and methyl p-toluate with a gas containing molecular oxygen esterifying the oxidation product with methanol, separating the resulting dimethyl terephthalate, and contacting the resulting residue (the distillation residue in the Witten process) with hydrogen in the presence of a hydrogenation catalyst until the substances in the residue are ring-saturated substantially completely, thereby to produce a compound having a cyclohexane ring (British Pat. No. 1,423,118).

The hydrogenation reaction in the third step of the process of this invention differs essentially from the above hydrogenation reaction in the conventional process in that in the third step of the present invention, the aromatic rings of the aromatic compounds present in the high-molecular-weight by-products do not undergo hydrogenation.

When ring hydrogenation occurs to form a compound having a cyclohexane ring, this compound is difficult to separate from the aromatic carboxylic acid or its methyl ester because it has similar physical properties to the aromatic carboxylic acid or its methyl ester. On the other hand, the aromatic carboxylic acid or its methyl ester is required generally to be of high purity, and the inclusion of impurities such as a compound having a cyclohexane ring should be avoided. Moreover, when ring hydrogenation occurs, the yield of the aromatic carboxylic acid or its methyl ester or precursors of any of these decreases. Hence, the ring hydrogenation should be avoided to the greatest possible extent.

In the third step of this invention, the contacting of the high-molecular-weight by-products with hydrogen is carried out so that the hydrogenation of the aromatic ring occurs only to an extent of not more than 5%, preferably not more than 1%. Most preferably, the contacting is carried out under conditions which do not substantially cause ring hydrogenation.

The hydrogenation reaction in the third step of this invention is carried out at a temperature of 80° to 350° C., preferably 120° to 330° C., especially preferably 150° to 300° C. At temperatures lower than 80° C., the high-molecular-weight by-products have a high viscosity and are difficult to treat, and moreover, the reaction is slow. At temperatures exceeding 350° C., undesirable sid-reactions occur to reduce the amounts of useful components such as dimethyl terephthalate.

Since the pressure of hydrogen greatly affects the ring hydrogenation, the partial pressure of hydrogen should be adjusted such that the ring hydrogenation of the aromatic compounds in the high-molecular-weight by-products does not substantially occur or occurs only to a limited extent. Preferably, the contacting of the high-molecular-weight by-products with hydrogen is carried out under a hydrogen partial pressure of 1 to 35 kg/cm$^2$, preferably 2 to 35 kg/cm$^2$. Generally, when the partial pressure of hydrogen exceeds 35 kg/cm$^2$, the hydrogenation of an aromatic ring tends to occur.

Suitable hydrogenation catalysts are, for example, nickel, copper-chromium, nobel metals such as palladium, platinum, rhodium and ruthenium. Palladium is preferred, and metallic palladium is especially preferred. The invention, however, is not limited to these specific catalysts, and any hydrogenation catalysts can be used which catalytically act on the hydrogenation of the high-molecular-weight by-products without inducing ring hydrogenation.

To prevent ring hydrogenation, it is effective to maintain the partial pressure of hydrogen at a low level. Another good method is to use a catalyst having a low ability to induce ring hydrogenation. For example, if a metallic palladium catalyst is somewhat poisoned to destroy its ring hydrogenating ability, and then used in the third step of the process of this invention, the hydrogenation reaction in accordance with this invention can be performed while limiting the ring hydrogenation reaction to an extent of nor more than 5% or without substantially inducing ring hydrogenation even when the partial pressure of hydrogen exceeds 35 kg/cm$^2$. When such a palladium/carbon catalyst having the reduced ability to induce ring hydrogenation is used, the reaction can be performed at a high hydrogen pressure, for example, at a hydrogen pressure of 1 to 100 kg/cm$^2$.

When metallic palladium is used as the hydrogenation catalyst, it is preferably supported on a carrier. In particular, it is advantageous to use it as supported on activated carbon. More favorable results can be obtained if the metallic palladium is supported in an amount of 0.01 to 15% by weight, especially 0.1 to 10% by weight, based on the activated carbon.

The hydrogenation reaction may be carried out while dispersing the hydrogenation catalyst in the high-molecular-weight by-products. It is convenient to render the hydrogenation catalyst into a granular form, pack it into a packed tower, and introduce the high-molecular-weight by-products and hydrogen through the catalyst layer (fixed bed).

The hydrogenation reaction can be performed either batchwise or continuously.

The amount of the catalyst used in this invention differs according to the reaction conditions such as temperature, pressure or treating time, and the type of the reactor used. For example, when the hydrogenation is performed batchwise, the amount of the catalyst is 1 ppm to 5000 ppm, preferably 5 ppm to 2000 ppm, as catalytic metal based on the starting material containing high-molecular-weight by-products. If the amount of the catalyst is smaller, the reaction becomes slow undesirably. There is no particular upper limit to the amount of the catalyst. But since the catalyst is expensive, too large an amount of it is commercially undesirable.

The contact-treating time differs according to the reaction temperature and pressure and the amount of the catalyst, but should be at least 1 minute. If the treating time is shorter, the conversion of the starting material is reduced. If the treating time is too long, the reactor must be made large-sized to cause economical disadvantage. Preferably, the treating time is up to 10 hours.

In the third step of the process of this invention, the high-molecular-weight by-products or the hydrogenation products thereof can be contacted and reacted with methanol during, before or after the hydrogenation reaction, as described in (A), (B) and (C) below.

(A) When the high-molecular-weight by-products are contacted with hydrogen and methanol in the presence of the hydrogenation catalyst, the hydrogenation reaction of the high-molecular-weight by-products and the decomposition and/or methyl-esterification thereof by methanol can be induced. This enables the desired aromatic carboxylic acid methyl ester and its useful precursors to be obtained in higher yields than in the case of performing hydrogenation alone.

Since at this time, the aromatic carboxylic acid and its useful precursors are prepared in the form of methyl esters, they can be separated and recovered from the reaction mixture by a simple means such as distillation.

The amount of methanol used for this purpose varies according to the variations of the constituents and proportions of the high-molecular-weight by-products and the method of charging methanol. Generally, it is at least 0.02 part by weight, preferably 0.05 to 10 parts by weight per part by weight of the starting material containing the high-molecular-weight by-products. It is commercially advantageous to perform the reaction while feeding methanol in the gaseous state into the reaction system.

If the high-molecular-weight by-products are contacted with hydrogen and methanol in the presence of the hydrogenation catalyst and in the presence of cobalt and/or manganese, the proportion of useful components which can be separated by distillation with relative ease, such as dimethyl terephthalate and methyl p-toluate, increases, and therefore, this procedure is more advantageous for commercial operations.

(B) In the third step of this invention, the high-molecular-weight by-products can be contacted with hydrogen in the presence of the hydrogenation catalyst, and then with methanol.

(C) Alternatively, the high-molecular-weight by-products can be contacted first with methanol, and then with hydrogen in the presence of the hydrogenation catalyst.

The amount of methanol and the manner of contacting it with the high-molecular-weight by-products in procedures (B) and (C) are the same as in the case of (A).

In either of (B) or (C), the desired aromatic carboxylic acid and its useful precursors can be obtained in the form of a methyl ester, and can be separated and recovered from the reaction mixture by a simple means such as distillation. Hence, these procedures are advantages over the case of performing only the hydrogenation reaction. Procedure (A) can afford the useful products in higher yields.

The contacting of the high-molecular-weight by-products in procedures (A), (B) and (C) can be performed under the same pressure conditions as in the hydrogenation reaction described hereinabove. The contacting of the by-products with methanol in (B) and (C) can be performed under the same temperature conditions as in the hydrogenation reaction in (A).

The following Examples illustrate the present invention without any intention of limiting the scope of the invention.

EXAMPLE A

A mixture of p-xylene and methyl p-toluate was oxidized with air in the liquid phase in the presence of cobalt acetate and manganese acetate at 165° C. and 4 kg/cm$^2$. G to afford an oxidation reaction product composed mainly of p-toluene acid and monomethyl terephthalate. The oxidation reaction product was esterified with methanol to form an exterification mixture consisting mainly of methyl p-toluene and dimethyl terephthalate.

The esterification mixture was distilled to separate compounds having lower boiling points than dimethyl terephthalate. Compounds having higher molecular weights than dimethyl terephthalate remained in the distillation residue. Since the distillation residue contained cobalt and manganese used in the oxidation reaction, they were recovered by extraction with water. The resulting distillation residue was distilled further to remove useful components such as dimethyl terephthalate and methyl p-toluate to give a residue almost free from useful components. The useful components remaining in this residue were only 1.0% of dimethyl terephthalate and 1.2% of monomethyl terephthalate.

A 500 cc stainless steel autoclave equipped with a stirrer was charged with 200 g of this distillation residue and 1 g of 5% by weight palladium/carbon. The inside of the autoclave was purged with nitrogen, and then several times with hydrogen. Hydrogen was blown into the autoclave under a partial pressure of 3 kg/cm$^2$.G at a flow rate at the exit of 500 cc/min. The autoclave was externally heated to 265° C., and the contents of the autoclave were maintained at this temperature for 1.5 hours with stirring. After the reaction, the autoclave was allowed to cool. The reaction product was taken out, and examined by composition analysis for the contents of p-xylene, dimethyl terephthalate, methyl p-toluate, methyl p-formylbenzoate, monomethyl terephthalate and p-toluic acid. The results are shown in Table 1 in the row of Run A-1.

For comparison, the same procedure as in Run A-1 was repeated except that nitrogen was introduced instead of hydrogen at a pressure of 3 kg/cm$^2$.G. The results are shown in Table 1 in the row of Run A-2.

The procedure of Run A-1 was also repeated except that the heating temperature was changed to 200° C.

(Run A-3), and that nitrogen was introduced instead of hydrogen (A-4; comparison). The results are also shown in Table 1.

toluic acid and monomethyl terephthalate. The results are shown in the column of Run C-1 in Table 3.

The above procedure was repeated except that the

TABLE 1

| Run | Temperature (°C.) | Pressure (kg/cm² · G) | Dimethyl terephthalate (g) | Monomethyl terephthalate (g) | Methyl p-toluate (g) | p-Toluic acid (g) | p-Xylene (g) | Total (g) |
|---|---|---|---|---|---|---|---|---|
| A-1 | 265 | 3 | 33.1 | 30.1 | 30.7 | 12.0 | 4.3 | 110.2 |
| A-2 (comp.) | 265 | 3(*) | 15.4 | 66 | 5.1 | 1.5 | — | 29.0 |
| A-3 | 200 | 3 | 17.3 | 33.0 | 40.5 | 13.8 | 3.3 | 107.9 |
| A-4 (comp.) | 200 | 3(*) | 2.0 | 2.5 | — | — | — | 4.5 |

(*)Nitrogen was introduced instead of hydrogen.

EXAMPLE B

A 500 cc stainless steel autoclave equipped with a feed opening, a refluxer, a condensate separator and a stirrer was charged with 200 g of the same distillation residue as obtained in Example A and 1 g of 5% palladium on carbon. The inside of the autoclave was purged with nitrogen, and then several times with hydrogen. Hydrogen was blown into the autoclave at a pressure of 3 kg/cm².G at a flow rate at the exit of 500 cc/min. The autoclave was heated externally to 265° C., and the reaction was performed for 1.5 hours with stirring. After the introduction of hydrogen, methanol was fed through the feed opening at a rate of 1.0 g/min. The reaction temperature was kept at 265° C., and the stirring was continued for 3 hours. After the reaction, the autoclave was allowed to cool. The product was taken out, and examined by composition analysis for the contents of p-xylene, dimethyl terephthalate, methyl p-toluate, methyl p-formylbenzoate, monomethyl terephthalate and p-toluic acid. The results are shown in Table 2.

The above procedure was repeated except that the treating temperature was changed to 200° C. The results are also shown in Table 2.

TABLE 2

| Items | Run B-1 | Run B-2 |
|---|---|---|
| Temperature (°C.) | 265 | 200 |
| Pressure (kg/cm² · G) | 3 | 3 |
| Dimethyl terephthalate (g) | 58.4 | 35.2 |
| Monomethyl terephthalate (g) | 7.0 | 17.7 |
| Methyl p-toluate (g) | 39.1 | 50.7 |
| p-Toluic acid (g) | 4.8 | 6.2 |
| p-Xylene (g) | 4.3 | 3.4 |
| Total (g) | 113.6 | 113.2 |

EXAMPLE C

A stainless steel autoclave equipped with a refluxer, a condensate separator, a stirrer, a methanol feed opening and a gas blow opening was charged with 200 g of the same distillation residue as obtained in Example A and 1 g of 5% palladium on carbon. While the contents of the autoclave were stirred at high speed at 250° C. and 10 kg/cm².G, hydrogen gas was blown into the autoclave at a flow rate at the exit of 500 cc/min. and simultaneously, methanol was introduced at a flow rate of 1.2 g/min. In this condition, the reaction was performed for 0.5 hour. After the reaction, the reaction mixture was weighed and analyzed to determine the contents of p-xylene, dimethyl terephthalate, methyl p-toluate, p- methanol was not introduced (Run C-2), and that nitrogen gas was blown into the autoclave instead of hydrogen (Run C-3). The results are also shown in Table 3.

TABLE 3

| Items | Run C-1 | Run C-2 | Run C-3 (comp.) |
|---|---|---|---|
| Temperature (°C.) | 250 | 250 | 250 |
| Pressure (kg/cm² · G) | 10 | 10 | 10(*) |
| Feed rate of methanol (g/min.) | 1.2 | 0 | 1.2 |
| Dimethyl terephthalate (g) | 37.6 | 5.5 | 31.7 |
| Monomethyl terephthalate (g) | 8.7 | 36.0 | — |
| Methyl p-toluate (g) | 57.8 | 45.9 | 2.1 |
| p-Toluic acid (g) | 5.8 | 15.8 | — |
| p-Xylene (g) | 5.5 | 2.0 | — |
| Total (g) | 115.4 | 105.2 | 43.8 |

(*)Nitrogen was introduced instead of hydrogen.

EXAMPLE D

A mixture of p-xylene and methyl p-toluate was oxidized in the liquid phase with air at 160° C. and 4 kg/cm².G in the presence of cobalt acetate and manganese acetate to form an oxidation product composed mainly of p-toluic acid and monomethyl terephthalate. The oxidation product was then esterified with methanol to afford an esterification mixture containing methyl p-toluate and dimethyl terephthalate as main products.

The esterfication mixture was distilled to separate compounds having lower boiling points than the dimethyl terephthalate. Compounds having higher molecular weights than dimethyl terephthalate remained in the distillation residue. Since the distillation residue contained cobalt and manganese used in the oxidation reaction, they were recovered by extraction with water. The distillation residue obtained was further distilled to remove useful components such as dimethyl terephthalate and methyl p-toluate which still remained. Thus, a distillation residue substantially free from the useful components was obtained. This distillation residue contained only 3.0% of dimethyl terephthalate and 1.5% of monomethyl terephthalate as useful components.

The same autoclave as used in Example C was charged with 200 g of the resulting distillation residue and a palladium catalyst. Hydrogen gas and methanol were simultaneously blown into the autoclave, and the reaction was performed for 0.5 hour with stirring at high speed.

The above procedure was repeated by varying the pressure, the temperature, the amount of the hydrogenation catalyst, the type of the carrier for the catalyst, the amount of the hydrogen off gas, and the amount of methanol fed. The results obtained are shown in Table 4.

| Run No. | Temperature (°C.) | Pressure (kg/cm² · G) | Amount of H₂ offgas (l/min.) | Amount of methanol (g/min.) | Hydrogenation catalyst | Amount of catalyst (g) | Total of useful components (g) |
|---|---|---|---|---|---|---|---|
| D-1 | 250 | 15 | 0.5 | 1.2 | 5% Pd/C | 0.5 | 105.6 |
| D-2 | " | 25 | " | " | " | " | 105.9 |
| D-3 | " | 30 | " | " | " | " | 103.2 |
| D-4 | 130 | 10 | " | " | " | " | 100.1 |
| D-5 | 300 | " | " | " | " | " | 107.0 |
| D-6 | 330 | " | " | " | " | " | 101.7 |
| D-7 | 250 | " | " | " | " | 0.05 | 88.3 |
| D-8 | " | " | " | " | " | 0.2 | 100.9 |
| D-9 | " | " | " | " | " | 1.0 | 105.4 |
| D-10 | " | " | " | " | 0.5% Pd/silica-alumina | 5.0 | 90.5 |
| D-11 | " | " | 0.2 | " | 5% Pd/C | 0.5 | 100.8 |
| D-12 | " | " | 2.0 | " | " | " | 105.4 |
| D-13 | " | " | 0.5 | 0.5 | " | " | 100.1 |
| D-14 | " | " | " | 2.0 | " | " | 104.8 |
| D-15 | " | " | " | 1.2 | 1% Pd/C | 1.0 | 101.3 |
| D-16 | " | " | " | " | 2% Pd/C | 1.0 | 105.2 |
| D-17 | " | " | " | " | 5% Pd, 5% Pt/C | " | 100.7 |
| D-18 | " | " | " | " | 5% Pd, 5% Ru/C | " | 97.8 |
| D-19 | " | " | " | 0 | Ni—P | 2.5 | 83.9 |

(Note)
*The composition and method for preparation of the Ni—P catalyst in Run D-19 were as follows:
Composition:
Ni 57.1% by weight
P 8.0% by weight
Oxygen 34.9% by weight
Method for Preparation:
Sodium hypophosphite monohydrate (60 g) and 45 g of nickel chloride were dissolved in 200 ml of water, and the solution was heated for 30 minutes under reflux. The resulting black powder was separated, washed with water, then with methanol and further with ether, and dried. This method is disclosed in Journal of the Chemical Society of Japan, Vol. 71, 626 (1968).

EXAMPLE E

An esterification mixture was prepared in the same way as in Example A. The esterification mixture was distilled to separate compounds having lower boiling points than dimethyl terephthalate. Compounds having higher molecular weights than dimethyl terephthalate remained in the distillation residue. This distillation residue contained 18.5% of dimethyl terephthalate, 2.8% of monomethyl terephthalate, 0.7% of methyl p-formylbenzoate, 0.4% of methyl p-toluate and 0.4% of p-toluic acid. It also contained 1240 ppm as metallic cobalt of the oxidation catalyst.

A stainless steel autoclave equipped with a refluxer, a condensate separator, a stirrer, a methanol feed opening and a gas blow inlet was charged with 200 g of the distillation residue and 1 g of 5% palladium on carbon. With stirring at high speed at 250° C. and 10 kg/cm².G, hydrogen was blown into the autoclave at a flow rate at the exit of 500 cc/min. Simultaneously, methanol was introduced at a flow rate of 1.2 g/min. In this condition, the reaction was performed for 0.5 hour. After the reaction, the reaction product was weighed and analyzed to determine the contents of p-xylene, dimethyl terephthalate, methyl p-toluate, p-toluic acid, and monomethyl terephthalate. The results are shown in Table 5 in the column of Run E-1.

The above procedure was repeated except that the methanol was not introduced (Run E-2). The results are also shown in Table 5.

TABLE 5

| Items | Run E-1 | Run E-2 |
|---|---|---|
| Dimethyl terephthalate (g) | 79.1 | 37.0 |
| Monomethyl terephthalate (g) | 1.8 | 30.3 |
| Methyl p-toluate (g) | 50.2 | 35.7 |
| p-Toluic acid (g) | 1.4 | 11.7 |
| p-Xylene (g) | 5.2 | 1.0 |
| Total (g) | 137.7 | 115.7 |

800 g of a product obtained by repeating the same experiment as Run E-1 was placed in a 1-liter three-necked flask, and distilled under reduced pressure to afford 565 g of a pale yellow distillate. Its gas chromatographic analysis showwed that it contained 312.4 g of dimethyl terephthalate, 1.1 g of monomethyl terephthalate, 201.1 g of methyl p-toluate, 2.3 g of p-toluate, and 19.0 g of p-xylene.

EXAMPLE F

A mixture of p-tolualdehyde and methyl p-toluate was oxidized in the liquid phase with air at 160° C. and 4 kg/cm².G in the presence of cobalt acetate and manganese acetate to form an oxidation product consisting mainly of p-toluic acid and monomethyl terephthalate. The oxidation product was then esterified with methanol to afford an esterification mixture containing methyl p-toluate and dimethyl terephthalate as main products.

The esterification mixture was distilled to separate compounds having lower boiling points than the dimethyl terephthalate. At this time, compounds having higher molecular weights than the dimethyl terephthalate remained in the distillation residue. Since the distillation residue contained cobalt and manganese used in the oxidation reaction, they were recovered by extraction with water. The distillation residue was further distilled to remove useful compounds such as dimethyl terephthalate and methyl p-toluate which still remained. Thus, a distillation residue subtantially free from the useful components was obtained. This distillation residue contained only 2.5% of dimethyl terephthalate and 1.5% of monomethyl terephthalate as useful components.

200 g of this distillation residue was charged into the same autoclave as used in Example E, and treated in the same way as in Example E.

The total amount of useful components such as dimethyl terephthalate, monomethyl terephthalate, methyl p-toluate and p-toluic acid which increased was 83.7 g per 200 g of the distillation residue.

EXAMPLE G

A mixture of p-xylene and methyl p-toluate was oxidized in the liquid phase with air at 170° C. and 4 kg/cm².G in the presence of cobalt acetate and manganese acetate to form an oxidation product containing p-toluic acid and monomethyl terephthalate as main components. The oxidation product was then esterified with methanol to afford an esterification mixture containing methyl p-toluate and dimethyl terephthalate as main products.

The esterification mixture was distilled to separate compounds having lower boiling points than the dimethyl terephthalate. At this time, compounds having higher molecular weights than the dimethyl terephthalate remained in the distillation residue. Since the distillation residue contained the heavy metal catalyst used in the oxidation reaction, it was recovered by extraction with water.

The resulting distillation residue was further distilled to remove useful components such as dimethyl terephthalate and methyl p-toluate which still remained. Thus, a distillation residue substantially free from the useful components was obtained.

The distillation residue contained only 2.8% by weight of dimethyl terephthalate as a useful component, and did not contain monomethyl terephthalate.

A 500 cc stainless steel autoclave equipped with a stirrer was charged with 200 g of the distillation residue and 3 g of 5% by weight palladium on carbon. Hydrogen was blown into the autoclave at a pressure of 10 kg/cm².G at a flow rate at the exit of 500 cc/min. The autoclave was heated externally to 250° C., and with stirring, the reaction was performed for 0.5 hour. (Run G-1).

The same procedure as above was repeated except that the pressure of hydrogen was changed to 40 kg/cm².G (Run G-2).

The results are shown in Table 6.

TABLE 6

| Items | Run G-1 | Run G-2 |
|---|---|---|
| Pressure (kg/cm² · G) | 10 | 40 |
| Dimethyl terephthalate (g) | 5.8 | 4.3 |
| Monomethyl terephthalate (g) | 35.8 | 10.3 |
| Methyl p-toluate (g) | 45.7 | 29.9 |
| p-Toluic acid (g) | 15.8 | 9.6 |
| p-Xylene (g) | 2.3 | 1.8 |
| Total of the useful components (g) | 105.4 | 55.9 |
| Other products | | |
| 4-Methylcyclohexanecarboxylic acid (g) | 0.1 | 10.7 |
| Methyl 4-methylcyclohexanecarboxylate (g) | 0.2 | 29.8 |
| Dimethyl 1,4-cyclohexanedicarboxylate (g) | not detected | 6.9 |

TABLE 6-continued

| Items | Run G-1 | Run G-2 |
|---|---|---|
| carboxylate (g) | detected | |

EXAMPLE H

A distillation residue substantially free from useful components was obtained by the same method as in Example A. This distillation residue contained 1.2% of dimethyl terephthalate and 1.2% of monomethyl terephthalate.

A cylindrical reactor having a diameter of 28 mm and a length of 175 mm was packed with 70 g of a bead-like 0.5% Pd/C catalyst, and maintained at 250° C. The distillation residue set forth above which had been heated to 250° C. in a preheater and methanol which had been also heated to 250° C. in a preheater were fed at a rate of 210 g/hr and 200 ml/hr respectively as an upwardly flowing stream. Hydrogen was passed through the reactor at a pressure of 10 kg/cm².G concurrent with the distillation residue and methanol. The reaction mixture obtained was separated into the reaction product, methanol and offgas by a gasliquid separator and a condenser. The flow rate of hydrogen was adjusted to 500 Nml/hr as the amount of the offgas. The reaction product and methanol were examined by composition analysis for the contents of useful components such as dimethyl terephthalate. This experiment was performed continuously for long periods of time. It was found that as shown in Table 7, the amounts of the useful components yielded scarcely changed even after a period of 200 hours.

TABLE 7

| Run No. | Treating time (hour) | Amount of useful components (g/200 g of the distillation residue) |
|---|---|---|
| H-1 | 1 | 103.4 |
| H-2 | 17 | 110.4 |
| H-3 | 41 | 113.7 |
| H-4 | 65 | 115.5 |
| H-5 | 89 | 105.3 |
| H-6 | 113 | 109.8 |
| H-7 | 137 | 115.2 |
| H-8 | 161 | 113.6 |
| H-9 | 185 | 103.2 |
| H-10 | 209 | 105.9 |

EXAMPLE I

A stainless steel autoclave equipped with a feed inlet opening, a stirrer and an opening for withdrawing the product was connected to a cylindrical reactor packed with 10 g of 0.5% palladium/carbon (beads with a diameter of 0.8 mm). A distillation residue (30 g/hr) obtained in the same way as in Example A and methanol (35 ml/hr) were fed by a pump from the feed inlet opening of the autoclave, and by high speed stirring, the methanol and the distillation residue were contacted with each other within the autoclave (with a residence time of 3 hours). The treated mixture was passed through the catalyst-packed reactor together with hydrogen as an upward flowing stream. During this time, the autoclave and the packed reactor were maintained at 260° C. and 25 kg/cm².G. The flow rate of hydrogen was adjusted to 200 cc/min. at the exit.

The mixture treated in the reactor was separated by a gas-liquid separator to obtain final products. The total amount of useful components such as dimethyl terephthalate was determined to be 114.8 g per 200 g of the starting distillation residue.

EXAMPLE J

A mixture of p-xylene and methyl p-toluate was oxidized in the liquid phase with air at 165° C. and 4 kg/cm$^2$.G in the presence of cobalt acetate and manganese acetate to afford an oxidation product consisting mainly of p-toluic acid and monomethyl terephthalate. p-Xylene was added to this product. The mixture was cooled, and then filtered to remove a part of terephthalic acid, monomethyl terephthalate and p-toluic acid. The filtrate was distilled to remove p-xylene and unreacted monomethyl p-toluate.

The resulting distillation residue contained only 9.3 g of p-toluic acid, and 18 g of monomethyl terephthalate as useful components per 200 g of residue. The same autoclave as used in Example C was charged with 200 g of the distillation residue and 1 g of 5% palladium/carbon, and it was reacted in the same way as in Run C-1 of Example C. After the reaction, the amounts of useful components which increased were measured by composition analysis. It was found that 82.1 g of useful components such as dimethyl terephthalate increased per 200 g of the starting distillation residue.

EXAMPLE K

The same procedure as in Example C, Run C-1 was repeated except that the oxidation was performed at 170° C. and 10 kg/cm$^2$.G using nickel acetate and manganese acetate instead of the cobalt acetate and manganese acetate as the oxidation catalyst. The total amount of useful components was 119.3 g.

The same procedure as above was repeated except that the oxidation was performed at 160° C. and 4 kg/cm$^2$.G using only cobalt acetate as the oxidation catalyst. The total amount of useful components was 23.5 g.

EXAMPLE L

Toluene was oxidized in the liquid phase with air at 165° C. and 10 kg/cm$^2$.G in the presence of cobalt acetate and manganese acetate to afford an oxidation product.

The oxidation product was distilled to separate benzoic acid and compounds having lower boiling points than benzoic acid. At this time, by-products having higher boiling points than benzoic acid remained in the distillation residue. Since the distillation residue still contained some amount of benzoic acid, it was recovered by extraction with hot water. The resulting purified residue scarcely contained useful components such as benzoic acid.

200 g of the purified residue was treated with hydrogen in the same way as in Example A, Run A-1. The results are shown in Table 8.

TABLE 8

|  | Toluene (g) | Benzoic acid (g) | Total (g) |
| --- | --- | --- | --- |
| Purified residue | — | 2.1 | 2.1 |
| Hydrogenated product | 30.1 | 26.8 | 56.9 |

EXAMPLE M p-Xylene was oxidized in the liquid phase with air at 180° C. and 15 kg/cm$^2$.G in the presence of cobalt acetate and manganese acetate to form an oxidation reaction product. The product was heat-treated at 240° C., and p-xylene was further added. The mixture was hot-filtered at 135° C. to separate terephthalic acid. The filtrate was distilled to remove p-xylene, p-toluic acid and compounds having lower boiling points than p-toluic acid. At this time, by-products having higher molecular weights than terephthalic acid remained in the distillation residue. Since the distillation residue still contained some p-toluic acid and the heavy metal catalyst used in the oxidation reaction, they were recovered by extraction with hot water.

The distillation residue scarcely contained useful components, and only contained 0.2% of terephthalic acid, and 1.0% of p-toluic acid as useful components.

200 g of the distillation residue was passed at a flow rate of 10 g/hr together with hydrogen through a reactor packed with 10 g of a bead-like 0.5% palladium-on-carbon catalyst. At this time, the reactor was maintained at 250° C. and 10 kg/cm$^2$.G, and the flow rate of hydrogen was adjusted such that the amount of it at the exit was 500 ml/min.

It was found by composition analysis that 49.7 g of terephthalic acid, 36.9 g of p-toluic acid, and 5.7 g of p-xylene was formed.

TABLE 9

| Products | Run M-1 |
| --- | --- |
| Terephthalic acid (g) | 49.7 |
| p-Toluic acid (g) | 36.9 |
| p-Xylene (g) | 5.7 |
| Total (g) | 92.3 |

EXAMPLE N

An apparatus for producing dimethyl terephthalate by the Witten-Hercules method was operated for long periods of time, and the amount of purified dimethyl terephthalate formed per day was determined (Run N-1). The results are shown in Table 10.

For comparison, the hydrogenation device in accordance with the process of this invention was not operated, and the distillation residue was discarded out of the system and burned. The amount of dimethyl terephthalate formed per day was measured, and is shown in Table 10. (Run N-2).

The apparatus used included:

an oxidation device for oxidizing a mixture of p-xylene and methyl p-toluate in the liquid phase with air;

an esterification device for esterifying the oxidation product consisting mainly of p-toluic acid and monomethyl terephthalate with methanol;

a distillation device for distilling the resulting esterification product under reduced pressure, and separating it into crude dimethyl terephthalate, compounds having lower boiling points than dimethyl terephthalate and the distillation residue;

a purifying device for purifying the resulting crude dimethyl terephthalate;

a vacuum-distillation device for recovering useful components such as dimethyl terephthalate still remaining in the distillation residue and the residue resulting from the purification, returning them to the main process thereby to obtain a distillation residue as distillation bottoms;

an extracting device for recovering the oxidation catalyst from the distillation residue; and a hydrogenation device for recovering the useful components from the distillation residue by the process of this invention and returning them to the main process.

TABLE 10

| Run | Hydrogenation device by the process of this invention | Amount of dimethyl terephthalate (parts by weight/day) |
| --- | --- | --- |
| N-1 | Operated | 133.9 |
| N-2 | Out of operation | 124.2 |

What is claimed is:

1. In a process for preparing an aromatic carboxylic acid or its methyl ester by oxidizing in the liquid phase with molecular oxygen or a gas containing molecular oxygen in the presence of a heavy metal catalyst at least one aromatic compound having at least one methyl or formyl group bonded to a ring carbon atom of the aromatic ring to form an oxidation product comprising said aromatic carboxylic acid, and, if desired, methyl-esterifying the oxidation product to form a methyl-esterification product comprising the methyl ester of said acid, and separating at least 70% by weight of the acid or the ester from the oxidation product or the methyl-esterification product, whereby a residue comprising by-products having higher molecular weights than the acid or the ester is formed, the improvement which comprises contacting said by-products with hydrogen in the presence of a hydrogenation catalyst to convert at least part of the by-products to the aromatic carboxylic acid or its methyl ester or precursors of said acid or ester, and recovering said acid or ester or precursors.

2. The process of claim 1 wherein the aromatic compound is an aromatic compound having a benzene, naphthalene or biphenyl ring.

3. The process of claim 1 wherein the aromatic compound is an aromatic compound having a benzene ring.

4. The process of claim 1 wherein the aromatic compound is toluene, p-xylene, p-toluic acid, p-tolualdehyde, methyl p-toluate, a mixture of p-xylene and methyl p-toluate, or a mixture of p-tolualdehyde and methyl p-toluate.

5. The process of claim 1 wherein the high-molecular-weight by-products are contacted with hydrogen and methanol in the presence of a hydrogenation catalyst.

6. The process of claim 1 wherein the high-molecular-weight by-products are contacted with hydrogen in the presence of a hydrogenation catalyst, and then with methanol.

7. The process of claim 1 wherein the high-molecular-weight by-products are contacted with methanol, and then with hydrogen in the presence of a hydrogenation catalyst.

8. The process of claim 1, wherein the hydrogenation catalyst is metallic palladium.

9. The process of claim 8 wherein the hydrogenation catalyst is metallic palladium supported on carbon as a carrier.

10. The process of claim 1, wherein the contacting of the high-molecular-weight by-products with hydrogen is carried out at a temperature of 80° to 350° C.

11. The process of claim 10 wherein the contacting of the high-molecular-weight by-products with hydrogen is performed at 120° to 330° C.

12. The process of claim 10 wherein the contacting of the high-molecular-weight by-products with hydrogen is carried out at a temperature of 150° to 300° C.

13. The process of claim 1, wherein the contacting of the high-molecular-weight by-products with hydrogen is performed under conditions such that the ring hydrogenation of the aromatic compounds in the high-molecular-weight by-products does not substantially take place.

14. The process of claim 13 wherein the contacting of the high-molecular-weight by-products with hydrogen is performed while the partial pressure of hydrogen is maintained at 1 to 35 $kg/cm^2.G$.

15. The process of claim 13 wherein the contacting of the high-molecular-weight by-products with hydrogen is performed while the partial pressure of hydrogen is maintained at 2 to 25 $kg/cm^2.G$.

16. The process of claim 1 wherein the high-molecular-weight by-products are a distillation residue containing components having higher molecular weights than dimethyl terephthalate which is obtained by oxidizing a mixture of p-xylene and methyl p-toluate in the liquid phase with a gas containing molecular oxygen in the presence of a heavy metal catalyst and in the absence of an alkanoic acid solvent and a halogen compound promotor, esterifying the oxidation reaction product with methanol, and separating substantially all or at least a part of dimethyl terephthalate and compounds having lower boiling points than dimethyl terephthalate by distillation from the resulting methyl-esterified product.

17. The process of claim 1 wherein the high-molecular-weight by-products are a residue containing components having higher molecular weights than terephthalic acid which is obtained by oxidizing p-xylene in the liquid phase with a gas containing molecular oxygen in the presence of a heavy metal catalyst and in the absence of an alkanoic acid solvent and a halogen compound promotor, and separating substantially all or a part of terephthalic acid from the oxidation reaction product.

18. The process of claim 1 wherein the high-molecular-weight by-products are a residue containing components having higher molecular weights than benzoic acid which is obtained by oxidizing toluene in the liquid phase with a gas containing molecular oxygen in the presence of a heavy metal catalyst and in the absence of an alkanoic acid solvent and a halogen compound promotor, and separating substantially all or a part of benzoic acid from the oxidation product.

19. The process of claim 1, wherein the heavy metal catalyst contains at least a manganese compound which is at least partially soluble in the oxidation reaction system.

20. The process of claim 1, wherein the heavy metal catalyst comprises at least (A) a manganese compound at least partially soluble in the oxidation reaction system and (B) a cobalt compound at least partially soluble in the oxidation reaction system.

21. The process of claim 1, wherein the heavy metal catalyst comprises at least (A) a manganese compound at least partially soluble in the oxidation reaction system and (C) a nickel compound at least partially soluble in the oxidation reaction system.

22. A process for making an aromatic carboxylic acid or its methyl ester or precursors thereof from the high-molecular-weight by-products fraction formed as by (a) oxidizing in the liquid phase with molecular oxygen or a gas containing molecular oxygen in the presence of a heavy metal catalyst at least one aromatic compound having at least one methyl or formyl group directly bonded to a ring carbon atom to form an oxidation reaction product comprising said acid, lower boiling components, and high-molecular-weight by-products, and, if desired, methyl-esterifying the oxidation reaction product to form a methyl-esterified oxidation reaction product comprising the methyl ester of said acid, lower boiling components, and high-molecular-weight by-products, and (b) separating substantially all of said acid and lower boiling components from said oxidation reaction product, or separating substantially all of said ester and lower boiling components from the methyl-esterified oxidation reaction product, which comprises treating said by-products fraction with hydrogen together with a hydrogenation catalyst.

* * * * *